US009763605B2

(12) United States Patent
Liu et al.

(10) Patent No.: US 9,763,605 B2
(45) Date of Patent: Sep. 19, 2017

(54) ADJUSTMENT OF SENSOR SENSITIVITY BY CONTROLLING COPOLYMER FILM THICKNESS THROUGH A CONTROLLED DRYING STEP

(71) Applicant: Verily Life Sciences LLC, Mountain View, CA (US)

(72) Inventors: Zenghe Liu, Alameda, CA (US); Huanfen Yao, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 834 days.

(21) Appl. No.: 14/092,655

(22) Filed: Nov. 27, 2013

(65) Prior Publication Data
US 2015/0148647 A1 May 28, 2015

(51) Int. Cl.
*H01M 4/04* (2006.01)
*A61B 5/145* (2006.01)
(Continued)

(52) U.S. Cl.
CPC ........ *A61B 5/14532* (2013.01); *A61B 5/1486* (2013.01); *A61B 5/6821* (2013.01); *G02C 7/04* (2013.01)

(58) Field of Classification Search
CPC ............. G01N 27/3274; G01N 27/327; G01N 27/3272; A61L 2/206; A61B 5/14532; A61B 5/14546; A61B 5/1486
See application file for complete search history.

(56) References Cited

U.S. PATENT DOCUMENTS

| 5,308,771 A | 5/1994 | Zhou et al. |
| 5,928,918 A | 7/1999 | Offenbacher |

(Continued)

FOREIGN PATENT DOCUMENTS

| WO | 01/57241 | 8/2001 |
| WO | 2012064179 A1 | 5/2012 |

OTHER PUBLICATIONS

International Searching Authority, International Search Report and Written Opinion for PCT/US2014/067621 mailed Feb. 26, 2015, 12 pages.

*Primary Examiner* — Gurpreet Kaur
(74) *Attorney, Agent, or Firm* — McDonnell, Boehnen, Hulbert, & Berghoff LLP

(57) ABSTRACT

An analyte sensor and a method for making the analyte sensor are disclosed. In one aspect, the analyte sensor includes a crosslinked, hydrophilic copolymer in contact with a surface of an electrode, and an analyte sensing component embedded within the crosslinked, hydrophilic copolymer. The method of making the analyte sensor includes depositing a precursor mixture containing monomers and an analyte sensing component onto an electrode, exposing the deposited precursor mixture to a controlled environment for a specified period of time, and photopolymerizing the deposited exposed precursor mixture into a copolymer layer in contact with a surface of the electrode. Exposing the deposited precursor mixture to a controlled environment can increase the sensitivity of the sensor by reducing the thickness of the copolymer layer and/or by causing the analyte sensitive component within the copolymer layer to have a non-uniform concentration within the layer.

25 Claims, 7 Drawing Sheets

(51) Int. Cl.
*G01N 33/50* (2006.01)
*A61B 5/1486* (2006.01)
*A61B 5/00* (2006.01)
*G02C 7/04* (2006.01)

(56) References Cited

U.S. PATENT DOCUMENTS

| | | |
|---|---|---|
| 6,653,358 B2 | 11/2003 | Bruza |
| 6,927,246 B2 | 8/2005 | Noronha |
| 7,731,826 B2 | 6/2010 | Hibbs |
| 8,224,414 B2 | 7/2012 | Kellogg |
| 8,385,998 B2 | 2/2013 | Zhang |
| 8,409,425 B2 | 4/2013 | Forrow |
| 8,437,829 B2 | 5/2013 | Mao |
| 2006/0234132 A1 | 10/2006 | Davidson et al. |
| 2007/0244379 A1* | 10/2007 | Boock ................ A61B 5/14532 600/345 |
| 2011/0136929 A1* | 6/2011 | Chow ................ A61B 5/14532 521/105 |
| 2012/0078070 A1 | 3/2012 | Liu et al. |
| 2012/0088997 A1* | 4/2012 | Guiseppi-Elie ........ A61B 5/145 600/364 |
| 2012/0107999 A1 | 5/2012 | Fan |
| 2012/0186997 A1 | 7/2012 | Li |
| 2012/0197231 A1 | 8/2012 | Kane et al. |
| 2012/0201755 A1 | 8/2012 | Rozakis et al. |
| 2012/0245444 A1 | 9/2012 | Otis |
| 2013/0011460 A1 | 1/2013 | Liu |
| 2013/0084649 A1 | 4/2013 | Crane |
| 2013/0164771 A1 | 6/2013 | Fukunaga et al. |

* cited by examiner

ADJUSTMENT OF SENSOR SENSITIVITY BY CONTROLLING COPOLYMER FILM THICKNESS THROUGH A CONTROLLED DRYING STEP

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. Electrochemical-based sensors are believed to be particularly suitable for the monitoring and quantification of analytes (e.g., glucose) in bodily fluid samples (e.g., blood, tear film, urine or interstitial fluid samples). The use of an electrochemical-based sensor that employs an analyte sensing component, (e.g., an enzyme) in conjunction with an electrode(s) allows for the quantification of an analyte in a liquid sample by detecting the product(s) produced from the reaction of the analyte sensing component and the analyte.

SUMMARY

In one aspect, a method is disclosed. The method involves depositing a mixture on a surface of an electrode, in which the mixture includes an analyte sensing component, an initiator, a first methacrylate monomer having a first hydrophilic side chain, a dimethacrylate monomer, and a second methacrylate monomer having a second hydrophilic side chain, where the initiator is sensitive to light. The method further involves exposing the deposited mixture to a controlled environment for a specified period of time and photopolymerizing the exposed deposited mixture to form a copolymer layer disposed on the surface of the electrode, where the photopolymerizing includes exposing the exposed deposited mixture to light.

In one aspect, an analyte sensor is disclosed. The analyte sensor includes an electrode and a layer on the surface of the electrode, where the layer includes a crosslinked hydrophilic copolymer and an analyte sensing component embedded within the crosslinked hydrophilic copolymer. The concentration of the analyte sensing component within the layer is non-uniform, such that the concentration is higher proximate the surface of the electrode. The crosslinked, hydrophilic copolymer has methacrylate-derived backbone chains of first methacrylate-derived units, second methacrylate-derived units and third methacrylate-derived units. The first and second methacrylate-derived units have side chains that can be the same or different and the third methacrylate-derived units in different backbone chains are connected by hydrophilic crosslinks.

These as well as other aspects, advantages, and alternatives, will become apparent to those of ordinary skill in the art by reading the following detailed description, with reference where appropriate to the accompanying drawings.

DETAILED DESCRIPTION

I. Overview

Figure 1A:
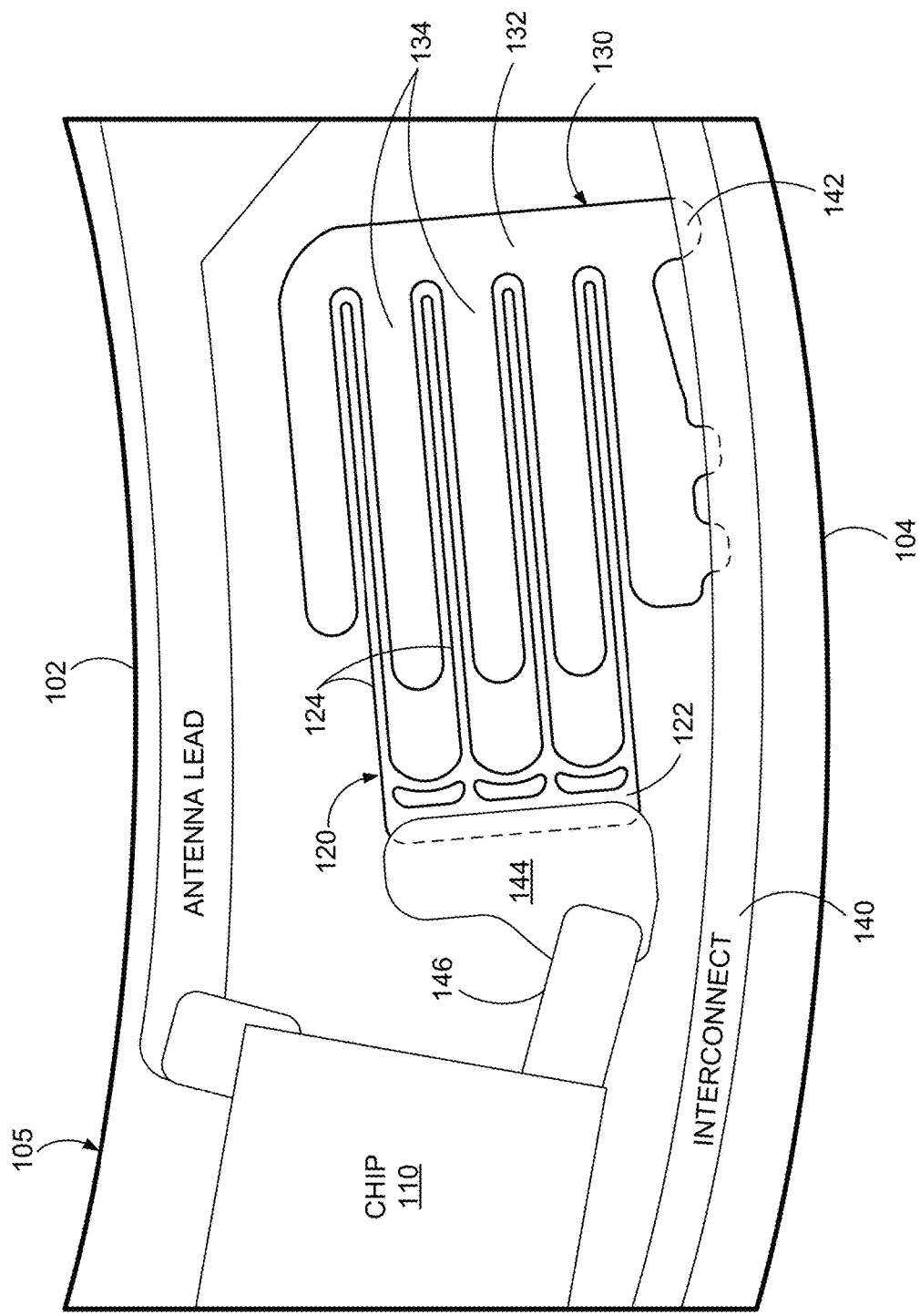
FIG. 1A illustrates an example arrangement for electrodes in an electrochemical analyte sensor disposed on a surface of a substrate.

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

The immobilization of an analyte sensing component in a copolymer can provide a sensor that could allow for the continuous or semi-continuous monitoring of one or more analytes. In an example, the sensor can include a crosslinked, hydrophilic copolymer having hydrophilic side chains and an enzyme immobilized or embedded within the copolymer. The hydrophilic side chains could form pores that allow the analyte of interest to contact and/or interact with the enzyme, resulting in the analyte undergoing a chemical reaction. The sensor could include an electrode, and the products of the enzyme-mediated reaction of the analyte could participate in an electrochemical reaction on or near the surface of the electrode. An electrical current could be generated from the electrochemical process and the current could be detected and used to quantify the amount of analyte present. For example, a sensor comprising a platinum electrode and a copolymer that is embedded with glucose oxidase can be used to determine a concentration of glucose in a system to which the sensor is exposed. The copolymer-embedded glucose oxidase could oxidize the glucose in the system, producing hydrogen peroxide. The hydrogen peroxide could undergo an electrochemical reaction at the platinum electrode, generating an electrical current. The electrical current could be used to determine the concentration of glucose in the system.

The sensitivity to an analyte of a sensor including an analyte sensing component embedded in a copolymer layer disposed on an electrode could depend on the thickness of the layer and/or the concentration of the enzyme in the layer. For example, a first sensor including an electrode, a copolymer layer having a first thickness, and an analyte-sensing component embedded in the copolymer layer could have a first sensitivity to the analyte. The first sensitivity to the analyte could be dependent on the ability of the analyte to diffuse through the layer and/or the ability of products of a reaction of the analyte to diffuse to the electrode. A second sensor could include an electrode, a copolymer layer, and an analyte-sensing component embedded in the copolymer layer, where the second sensor is configured similarly to the first sensor except that the copolymer layer has a second thickness less than the first thickness. The second sensor could have a second sensitivity to the analyte that was greater than the first sensitivity; this could be due to the decreased thickness of the layer of the second sensor resulting in an increased ability of the analyte to diffuse through the layer of the second sensor to the analyte sensing component and/or an increased ability of products of a reaction of the analyte (where the reaction is mediated by the analyte-sensing component) to diffuse to the electrode of the second sensor.

In another example, a first sensor including an electrode, a copolymer layer, and an analyte-sensing component embedded in the copolymer layer could have a first sensitivity to the analyte. The analyte-sensing component has a concentration that is uniform throughout the copolymer layer. The first sensitivity to the analyte could be dependent on the ability of the analyte to diffuse through the layer and/or the ability of products of a reaction of the analyte to diffuse to the electrode. A second sensor could include an electrode, a copolymer layer, and an analyte-sensing component embedded in the copolymer layer, where the second sensor is configured similarly to the first sensor except that the analyte-sensing component has a non-uniform concentration in the layer and the concentration of the analyte-sensing component is higher proximate the electrode. The second sensor could have a second sensitivity to the analyte that was greater than the first sensitivity; this could be due to the increased concentration of the analyte-sensing component proximate the electrode resulting in an increased ability of products of a reaction of the analyte (where the reaction is mediated by the analyte-sensing component) to diffuse to the electrode of the second sensor.

A sensor as described above could be made according to a method. The method could include forming a mixture including an analyte-sensing component, a first monomer, a second monomer, a crosslinking agent and a light-sensitive initiator; depositing the mixture on an electrode; exposing the deposited mixture to a controlled environment for a specified period of time; and photopolymerizing the exposed deposited mixture such that the exposed deposited mixture forms a copolymer layer disposed on the electrode. In some examples, the specified time and a property or properties of the controlled environment could be chosen to affect the thickness of the copolymer layer. In some examples, the specified time and a property or properties of the controlled environment could be chosen to affect a concentration of the analyte-sensing component in the copolymer and/or to affect a concentration gradient of the analyte sensing component in the copolymer. In some examples, the specified time and a property or properties of the controlled environment could be chosen to affect the sensitivity of the sensor. The mixture could be made with phosphate buffered saline. Photopolymerizing the exposed deposited mixture could include exposing the exposed deposited mixture to ultraviolet light.

II. Example Analyte Sensors

An analyte sensor could include an electrode and a layer disposed on the surface of the electrode. The layer could include a crosslinked, hydrophilic copolymer and an analyte sensing component embedded in the copolymer, where the analyte-sensing component has a non-uniform concentration within the layer such that the concentration of the analyte-sensing component is higher proximate to the electrode.

In some embodiments, the analyte sensor is an enzyme-based biosensor. Such analyte sensors could be able to convert a rate of an analyte-concentration-dependent biochemical reaction into a measurable physical signal, such as an optical or electrical signal. The analyte-concentration-dependent biochemical reaction could be mediated by the analyte sensing component. The analyte sensing component could be an enzyme that reacts selectively with the analyte. Such an analyte sensor could be used in the detection of analytes in clinical, environmental, agricultural and biotechnological applications. Analytes could be measured in clinical assays of fluids of the human body; such analytes could include glucose, lactate, pyruvate, urea, retinal/vitamin A, cholesterol, bilirubin, proteins, lipids, electrolytes or any other analyte according to an application. The detection of analytes in biological fluids, such as blood, tear film, or intestinal fluid, could be used for the diagnosis and the monitoring of many diseases.

The analyte sensing component could be embedded in a polymer network of the crosslinked, hydrophilic copolymer. The embedded analyte sensing component could be immobilized in the copolymer and could interact with a corresponding analyte of interest. In some embodiments, the analyte sensing component includes an enzyme.

The analyte sensing component of the analyte sensor could be selected to monitor physiological levels of a specific analyte in a fluid to which the analyte sensor is exposed. For example, glucose, lactate, cholesterol and various proteins and lipids can be found in body fluids, including, for example, tear film, and can be indicative of medical conditions that could benefit from continuous or semi-continuous monitoring.

The analyte sensing component can be an enzyme selected to enable the analyte sensor to monitor one or more analytes. For example, physiological cholesterol levels could be monitored with cholesterol oxidase, lactate levels with lactate oxidase, and glucose levels with glucose oxidase or glucose dehydrogenase (GDH).

In some embodiments, the analyte sensing component can be an enzyme that mediates a chemical reaction of an analyte to produce detectable reaction products. For example, an analyte sensor could include a crosslinked, hydrophilic copolymer layer situated proximate a working electrode. Glucose oxidase ("GOx") could be embedded in the copolymer layer and could catalyze a reaction of glucose to produce hydrogen peroxide ($H_2O_2$). As shown below, the hydrogen peroxide could then be oxidized at the working electrode, releasing electrons to the working electrode, generating a current.

$$\text{glucose} + O_2 \xrightarrow{\text{GOx}} H_2O_2 + \text{gluconolactone}$$
$$H_2O_2 \longrightarrow 2H^+ + O_2 + 2e^-$$

The current generated by either reduction or oxidation reactions at the working electrode can be approximately proportionate to the reaction rate. Further, the reaction rate can be dependent on the rate of analyte molecules reaching the working electrode to fuel the reduction or oxidation reactions, either directly or catalytically through a reagent. In a steady state, where analyte molecules diffuse to the working electrode from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

In some embodiments, the analyte sensing component is glucose dehydrogenase (GDH). In certain instances, a selected analyte sensing component can require cofactors in order to sense the analyte. The cofactors could be embedded in the copolymer layer of the analyte sensor with the analyte sensing component. Cofactors could include flavin adenine dinucleotide (FAD), thiamine pyrophosphate (TPP), nicotinamide adenine dinucleotide (NAD), flavin mononucleotide (FMN), pyrroloquinoline quinone (PQQ) or a coenzyme. In embodiments incorporating glucose oxidase, FAD could be included. In embodiments incorporating pyruvate oxidase, FAD and TPP could be included.

An analyte sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which a reference electrode serves as a counter-electrode. The working electrode can be connected to the reference electrode via a circuit, such as a potentiostat.

FIG. 1A illustrates an example arrangement for electrodes in an analyte sensor disposed on a surface of a substrate. FIG. 1A illustrates a portion of a substrate 105 on which an electrochemical analyte sensor is mounted. The substrate 105 is configured to be embedded in an eye-mountable device and can be similar to the substrate 220 described below in connection with FIG. 2. The substrate 105 can be shaped as a flattened ring with an inner edge 102 and an outer edge 104. The two edges 102, 104 may both be at least approximately circular, although only a portion of each is shown in FIG. 1A.

The substrate 105 provides a mounting surface for mounting a chip 110 and for patterning sensor electrodes, an antenna, and conductive interconnects between pads or terminals on the chip 110 and the other components. An electrochemical analyte sensor could include a working electrode 120 and a reference electrode 130 patterned in an interdigitated arrangement. The working electrode 120 could include four fingers 124 that can each have a relatively narrow width (e.g., about 25 micrometers) and that extend from a base 122. The working electrode 120 is electrically connected to a connection pad of the chip 110 through a pair of overlapped interconnects 144, 146. The reference electrode 130 includes fingers 134 that extend from a base 132. As shown in FIG. 1A, the fingers 124, 134 of the two electrodes 120, 130 can be at least approximately parallel with one another. Moreover, the electrodes 120, 130 can be arranged in an interdigitated arrangement such that each of the fingers 124 of the working electrode 120 is interposed between two of the fingers 134 of the reference electrode in an at least approximately symmetric manner. As such, each of the working electrode fingers 124 can have a similar voltage gradient along both opposing side edges. The reference electrode 130 can then be electrically connected to another pad (not visible) on the chip 110 via the interconnect 140 that connects to the reference electrode 130 at multiple overlap points 142.

The chip 110 can also be connected to other components via additional connection pads. For example, as shown in FIG. 1A, the chip 110 can be connected to an antenna lead, which can be formed of a patterned conductive material, such as electroplated gold, for example, that substantially circles the substrate 105 to create a loop antenna.

Figure 1B:
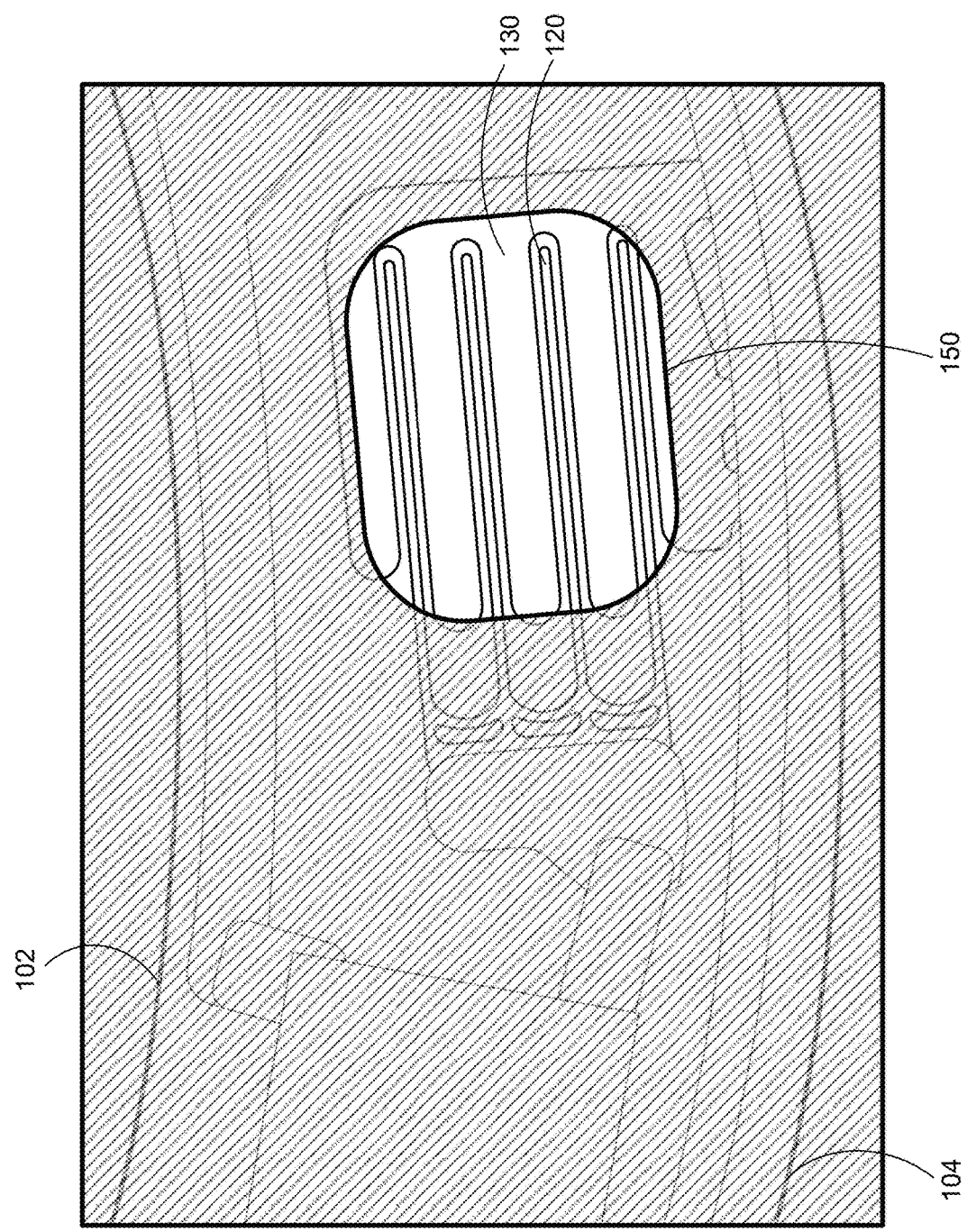
FIG. 1B illustrates the arrangement in FIG. 1A when embedded in a polymeric material with a channel positioned to expose the electrochemical analyte sensor electrodes.

FIG. 1B illustrates the arrangement in FIG. 1A when embedded in a polymeric material with a channel 150 positioned to expose the electrochemical sensor electrodes 120, 130. In FIG. 1B, the polymeric material is illustrated by the hash pattern that is superimposed over the portion of the substrate 105 shown in FIG. 1A. The channel 150 may be formed by removing a portion of the encapsulating polymeric material (e.g., by etching, by removing a layer defined by a photoresist, etc.). The channel 150 exposes a region including the sensor electrodes 120, 130, such that tear film coating the polymeric material is able to contact a copolymer layer (not shown) disposed on the sensor electrodes 120, 130, and an analyte in the tear film is able to interact with an analyte sensing component in the copolymer layer. Results of the interaction between the analyte and the analyte sensing component can be sensed at the electrodes 120, 130. The exposed region created by the channel 150 can include a desired cumulative length of the working electrode 120 (e.g., a cumulative length of approximately 1000 micrometers). The exposed area of the reference electrode can be at least five times the exposed area of the working electrode, so that the half-cell potential of the reference electrode is substantially stable while making amperometric measurements.

In the sensor electrode arrangement shown in FIG. 1A-1B in which the electrodes are mounted on the substrate 105, the extended fingers 124, 134 of the two electrodes 120, 130 are each oriented at least approximately tangential to the side edges 102, 104 of the substrate. In other words, the interdigitated fingers 124, 134 have lengths that are locally parallel to the side edges 102, 104. As such, the electrodes 120, 130 are more able to comply with curvature in the substrate 105. Arranging the electrode fingers 144, 134 to be locally parallel to the side edges causes each of the electrode fingers 124, 134 to be located along a single radius of curvature, even as the substrate 105 conforms to a convex curvature of an eye-mountable device (or adjusts to stresses or strains of being contact-mounted to an eye or of some other application). For example, if the substrate 105 is curved to comply with the concave curvature of an eye-mountable device in which the substrate 105 is embedded, the individual finger extensions 124, 134 can conform to the local radius of curvature at each location without substantially influencing the inter-electrode spacing. By contrast, an arrangement with finger extensions that cross multiple radii of curvature may be urged to adjust its inter-electrode spacing in a non-uniform manner, along the length of the finger extensions.

While not specifically illustrated in FIG. 1A-1B, the electrochemical analyte sensor includes a crosslinked, hydrophilic copolymer layer that immobilizes a suitable analyte sensing component near the working electrode 120 so as to sensitize the electrochemical analyte sensor to an analyte. In some examples, this copolymer layer takes the form of an analyte-permeable copolymer layer disposed on the working electrode in the channel 150 positioned to expose the electrochemical analyte sensor to a tear film. The copolymer layer can be created from a chemical mixture including 2-hydroxyethyl methacrylate, di(ethylene glycol) dimethacrylate, 2,2-dimethoxy-2-phenylacetophenone, and poly(ethylene glycol) methyl ether methacrylate. The analyte sensing component embedded within the copolymer layer could be an enzyme that interacts selectively with the analyte. In some embodiments, the analyte is glucose and the analyte sensing component could include glucose oxidase. The glucose oxidase could react with glucose that has diffused into the copolymer layer from the tear film to which the analyte sensor is exposed, creating at least hydrogen peroxide. In some examples, the sensor electrodes 120, 130 comprise platinum, and the hydrogen peroxide is sensed amperometrically by applying a voltage of +400 mV to +500 mV to the working electrode 120 relative to the reference electrode 130 and then measuring the current through the working electrode 120. The embodiments above are meant only as illustrative examples; other copolymer layer compositions, analytes, analyte sensor platforms, analyte sensing components, electrode materials, and amperometric voltages are anticipated.

Moreover, it is particularly noted that while an example analyte sensor is described herein by way of example as an eye-mountable device or an ophthalmic device, it is noted that the disclosed analyte sensor and electrode arrangements therefore can be applied in other contexts as well. For example, analyte sensors disclosed herein may be included in wearable (e.g., body-mountable) and/or implantable analyte sensors. In some contexts, an analyte sensor is situated to be substantially encapsulated by bio-compatible polymeric material suitable for being in contact with bodily fluids and/or for being implanted. In one example, a mouth-mountable device includes an analyte sensor and is configured to be mounted within an oral environment, such as adjacent a tooth or adhered to an inner mouth surface. In another example, an implantable medical device that includes an analyte sensor may be encapsulated in biocompatible material and implanted within a host organism. Such body-mounted and/or implanted analyte sensors can include circuitry configured to operate an amperometric electrochemical sensor by applying a voltage across sensor electrodes in the analyte sensor and measuring a resulting current. The analyte sensor can also include an energy harvesting system and a communication system for wirelessly indicating the sensor results (e.g., measured current). Electrochemical analyte sensor electrodes can also be substantially co-planar and the working electrode can include relatively narrow extensions that are interdigitated with respect to the portions of the reference electrode. The analyte sensor electrodes can be symmetrically arranged with a working electrode substantially surrounded by portions of a reference electrode such that voltage gradients along opposing side edges of the working electrode are substantially symmetric. The sensor electrodes in such amperometric electrochemical analyte sensors can be arranged similarly to any of the symmetrically arranged electrodes disclosed above in connection with the example devices described in connection with FIGS. 1A-1B.

In other examples, analyte sensors disclosed herein may be included in analyte sensors which are not used to measure an analyte concentration in or on a human body. For example, analyte sensors disclosed herein may be included in body-mountable and/or implantable analyte sensors used to measure an analyte concentration in a fluid of an animal. In another example, analyte sensors disclosed herein may be included in devices to measure a retinal concentration in an environmental fluid, such as a fluid in a river, lake, marsh, reservoir, water supply, sanitary sewer system, or storm sewer system. In another example, analyte sensors disclosed herein may be included in devices to measure a retinal concentration in a fluid which is part of a process, such as a waste treatment process, pharmaceutical synthesis process, food preparation process, fermentation process, or medical treatment process An electrode included in the analyte sensor can be formed from any type of conductive material and can be patterned by any process that be used for patterning such materials, for example deposition or photolithography, according to an application. The conductive materials can be, for example, gold, platinum, palladium, titanium, carbon, copper, silver/silver-chloride, conductors formed from noble materials, metals, or any combinations of these materials. Other materials can also be envisioned.

The analyte sensing material embedded in the copolymer layer could be distributed within the copolymer layer according to an application. In some examples, the analyte sensing component could be evenly distributed within the copolymer layer, having a concentration that is uniform throughout the copolymer layer. In some examples, the analyte sensing component could be unevenly distributed within the copolymer layer. For example, the analyte sensing component could have a concentration profile in the layer such that there was a higher concentration of the analyte sensing component in the copolymer layer proximate the electrode and a lower concentration of the analyte sensing component in the copolymer layer farther from the electrode The thickness of the crosslinked, hydrophilic copolymer layer of the analyte sensor can vary depending on the desired properties of the analyte sensor. The thickness of the copolymer layer, as measured from the top of the electrode to the top of the copolymer, can affect the flow of the analyte to the analyte sensing component. Depending on the characteristics of the copolymer layer, the type of analyte sensing component used, and the analyte to be monitored, the thickness of the copolymer layer can be chosen such that the analyte sensor has a desired sensitivity to the analyte. That is, thicker copolymer layers could reduce the rate, for a given concentration of the analyte in a fluid to which the analyte sensor is exposed, at which the analyte diffused from the fluid to the analyte sensing component. A thinner thickness of the copolymer layer could be chosen to increase the rate, for a given concentration of the analyte in the fluid, that the analyte diffuses to the analyte sensing component, thus increasing the sensitivity of the analyte sensor. In some instances, the thickness of the copolymer layer could be from less than about 10 µm to about 30 µm. In some instances, the copolymer is less than 20 µm in thickness, where in other applications the copolymer is about 20 µm to about 25 µm in thickness. In certain applications, the copolymer is about 10 µm to about 15 µm in thickness, where in other applications the copolymer is about 15 µm to about 20 µm or about 25 µm to about 30 µm in thickness. In some embodiments, the copolymer is about 20 µm in thickness.

The crosslinked, hydrophilic copolymer layer of the analyte sensor can include backbone chains of methacrylate-derived units, and an analyte sensing component, such as an enzyme, embedded within the copolymer. The methacrylate-derived units can include first and second methacrylate-derived units. Each of the first and second methacrylate-derived units of the backbones could be covalently bound independently to first and second hydrophilic side chains, respectively. The crosslinked, hydrophilic copolymer layer can also include third methacrylate units. Each of the third methacrylate-derived units can be covalently bound through a crosslink to another third methacrylate-derived unit in a different backbone chain. The crosslinks, or groups through which the third methacrylate-derived units can be connected, are discussed in greater detail below. Various conformations and compositions of the side chains of the first and second methacrylate-derived units, and the crosslinks of the third methacrylate-derived units could be used to adjust the properties of the crosslinked, hydrophilic copolymer layer as desired. These properties of the crosslinked, hydrophilic copolymer layer could include hydrophilicity, permeability to an analyte or analytes, and ability to immobilize an analyte sensing component.

The side chains of the first and second methacrylate-derived units can be hydrophilic, and can be water soluble or soluble in a water-miscible solvent, such as an alcohol. The side chains can have one or more heteroatoms, for example, nitrogen, oxygen or sulfur atoms. In some embodiments, the side chains have one or more hydroxy groups.

In some embodiments, the side chains of the first and second methacrylate-derived units include one or more alkylene oxide units. The alkylene oxide units can be in the form of a polymer, such as poly(ethylene glycol), poly(propylene glycol), poly(butylene oxide), or a mixture thereof. The alkylene oxide unit polymer can be a copolymer including a combination of two or three different alkylene oxide units. In some embodiments, the poly(alkylene oxide) of the side chains is a block copolymer including blocks of two or three different poly(alkylene oxide) polymers. In certain embodiments, the poly(alkylene oxide) is block copolymer of poly(ethylene glycol) and poly(propylene glycol). In other embodiments, the second side chain and the crosslinks both include poly(ethylene glycol).

In some embodiments, the first methacrylate-derived units can have the structure of formula (I):

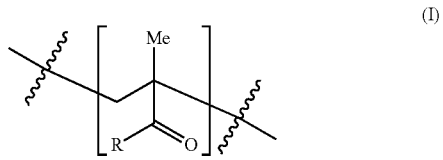

(I)

where R is a hydrophilic group. In certain embodiments, the hydrophilic group includes one or more hydroxy groups, such as an alcohol moeity.

In some embodiments, the first methacrylate-derived units can have the structure of formula (Ia):

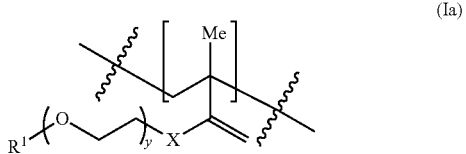

(Ia)

where X is —O—, —NR'— or —S—, y is 0, 1, 2, 3, 4, 5, 6, 7, 8, 9 or 10, and $R^1$ is hydrogen, —$C_1$-$C_{12}$alkyl, —$C_1$-$C_{12}$alkyl-OH, —SiR'$_3$, —C(O)—$C_1$-$C_{12}$alkyl, —$C_1$-$C_{12}$alkyl-C(O)OR', where R' is —$C_1$-$C_{12}$alkyl.

In certain embodiments, the first methacrylate-derived units can have the structure:

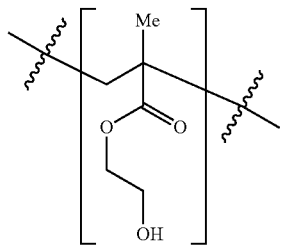

In some embodiments, the second methacrylate-derived units can have the structure of formula (II):

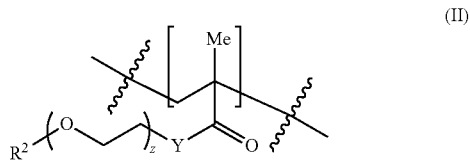

(II)

where Y is —O—, —NR'— or —S—, z is 0, 1, 2, 3, 4, 5, 6, 7, 8, 9 or 10, and $R^2$ is hydrogen, —$C_1$-$C_{12}$alkyl, —SiR'$_3$, —C(O)—$C_1$-$C_{12}$alkyl, —$C_1$-$C_{12}$alkyl-C(O)OR', where R' is hydrogen or —$C_1$-$C_{12}$alkyl.

In certain embodiments, the second methacrylate units can have a number of different values for z. In certain embodiments, the second methacrylate units have a number of different values for z and an average value of z, by number of units, is an average value of from about 2 to about 250.

In some embodiments, the second methacrylate-derived units can have the structure of formula (IIa):

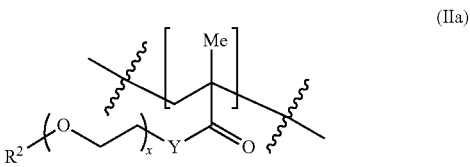

(IIa)

where Y and $R^2$ are as described above and x has a number of different values such that the poly(ethylene glycol) component of the second methacrylate units has a number average molecular weight ($M_n$) of about 100 daltons to about 10,000 daltons. In certain embodiments, the values for x are selected so that the $M_n$ of the poly(ethylene glycol) component falls within a range in Table 1.

TABLE 1

| $M_n$ range in daltons of poly(ethylene glycol) component in the second methacrylate-derived units (values are approximate). | |
|---|---|
| Low | High |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the analyte sensor can have second methacrylate-derived units having the structure of formula (IIa), where Y is —O—, $R^2$ is methyl and x has a number of different values such that the poly(ethylene glycol) component of the second methacrylate units has a number average molecular weight ($M_n$) of about 500 daltons.

In some embodiments, the presence of the second methacrylate-derived units having second hydrophilic side chains in the crosslinked, hydrophilic copolymer layer of the analyte sensor could form a porous network. The structure of the porous network could include regions within the copolymer layer that are not occupied by copolymer material, these regions are referred to herein as "pores". Controlling a property or properties of the porous network of the crosslinked, hydrophilic copolymer layer could facilitate control of the equilibrium between the concentration of the analyte (e.g., glucose) in a sample solution, and the analyte concentration in the proximity of the analyte sensor electrode surface. When all of the analyte arriving at the analyte sensor is consumed, the measured output signal could be linearly proportional to the flow of the analyte into the analyte sensor and thus to the concentration of the analyte in the sample solution. However, when the analyte consumption is limited by the kinetics of chemical, electrochemical, or diffusive activities in the analyte sensor, the measured output signal could no longer be controlled by the flow of analyte into the analyte sensor and could be no longer linearly proportional to the concentration of the analyte in the sample solution. In this case, only a fraction of the analyte arriving at the analyte sensing component is consumed before the analyte sensor becomes saturated, whereupon the measured signal from the electrode could stop increasing, or could increase only slightly, with an increasing concentration of the analyte in the sample solution. The porous network could control the flow of the analyte from the sample solution to the analyte sensing component so that the sensor does not become saturated and could therefore enable a wider range of analyte concentrations in the sample solution to be measured.

The hydrophilic properties of the second side chain of the second methacrylate-derived units could be chosen to produce desired properties of the porous network, such as a desired permeability of the copolymer layer to the analyte. For example, flow of the analyte into or across the sensor could be dependent on the specific analyte being monitored; thus, the porous network could be configured to obtain properties for monitoring a specific analyte in the sample solution. In some applications, the hydrophilicity of the porous network could be adjusted by changing the number of alkylene oxide units in the second side chain. In some examples, the hydrophilicity of the porous network could be controlled by specifying the ratio of carbon atoms (i.e., —C—, —CH—, —CH$_2$— or —CH$_3$) to alkylene oxide units in the side chain of the second methacrylate-derived units.

The crosslinks of the crosslinked, hydrophilic copolymer layer that connect the third methacrylate-derived units in different backbone chains, and the third methacrylate units, and are represented by "A" in formula (III):

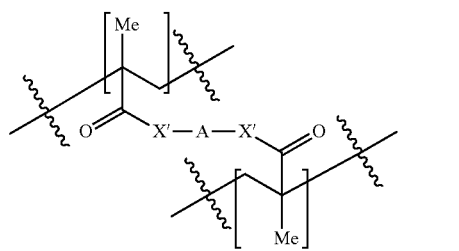

(III)

where X' is independently —O—, —NR'— or —S—, and A is a hydrophilic group.

In some embodiments, the crosslinks are hydrophilic. The crosslinks could be soluble in water or a water-miscible solvent, such as an alcohol. The crosslinks could have one or more heteroatoms, for example, nitrogen, oxygen or sulfur atoms. In some embodiments, the crosslinks could have one or more hydroxy groups.

In some embodiments, the crosslinks include one or more alkylene oxide units. The alkylene oxide units could be in the form of a polymer, such as poly(ethylene glycol), poly(propylene glycol), poly(butylene oxide) or a mixture thereof. The alkylene oxide unit polymer can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks and the second methacrylate-derived units include poly(ethylene glycol).

In some embodiments, the crosslinks can include one or more ethylene oxide units. For example, the crosslinks (e.g., A in formula (III) above) can have the structure of formula (IIIa):

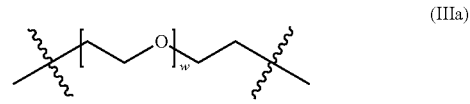

(IIIa)

where w is 0, 1, 2, 3, 4, 5, 6, 7, 8, 9 or 10.

In certain embodiments, the crosslinks can have a number of different values for w. In certain embodiments, the crosslinks have a number of different values for w and an average value w, by number of crosslinks, is an average value of from about 2 to about 250.

In some embodiments, the crosslinks of formula (IIIa) have a number of different values for w such that the poly(ethylene glycol) component (within the brackets in formula (IIIa)) of the crosslinks has a number average molecular weight ($M_n$) of about 100 daltons to about 10,000 daltons. For example, the values for w can be selected such that the $M_n$ of the poly(ethylene glycol) component of the crosslinks falls within a range in Table 2:

TABLE 2

| $M_n$ range in daltons of the poly(ethylene glycol) component of the crosslinks (values are approximate). ||
|---|---|
| Low | High |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |

TABLE 2-continued

M$_n$ range in daltons of the poly(ethylene glycol) component of the crosslinks (values are approximate).

| Low | High |
|---|---|
| 9,000 | 10,000 |

In some embodiments, the crosslinks and third methacrylate units are derived from di(ethylene glycol) dimethacrylate, such that w is 1.

In some embodiments, the analyte sensor could be a component of a body-mountable device, such as an eye-mountable, tooth-mountable, or skin-mountable device. The eye-mountable device could be configured to monitor health-related information based on one or more analytes detected in a tear film (the term "tear film" is used herein interchangeably with "tears" and "tear fluid") of a user wearing the eye-mountable device. For example, the eye-mountable device could be in the form of a contact lens that includes a sensor configured to detect one or more analytes (e.g., glucose, pyruvate, urea, retinal/vitamin A). The eye-mountable device could also be configured to monitor various other types of health-related information.

Figure 2A:
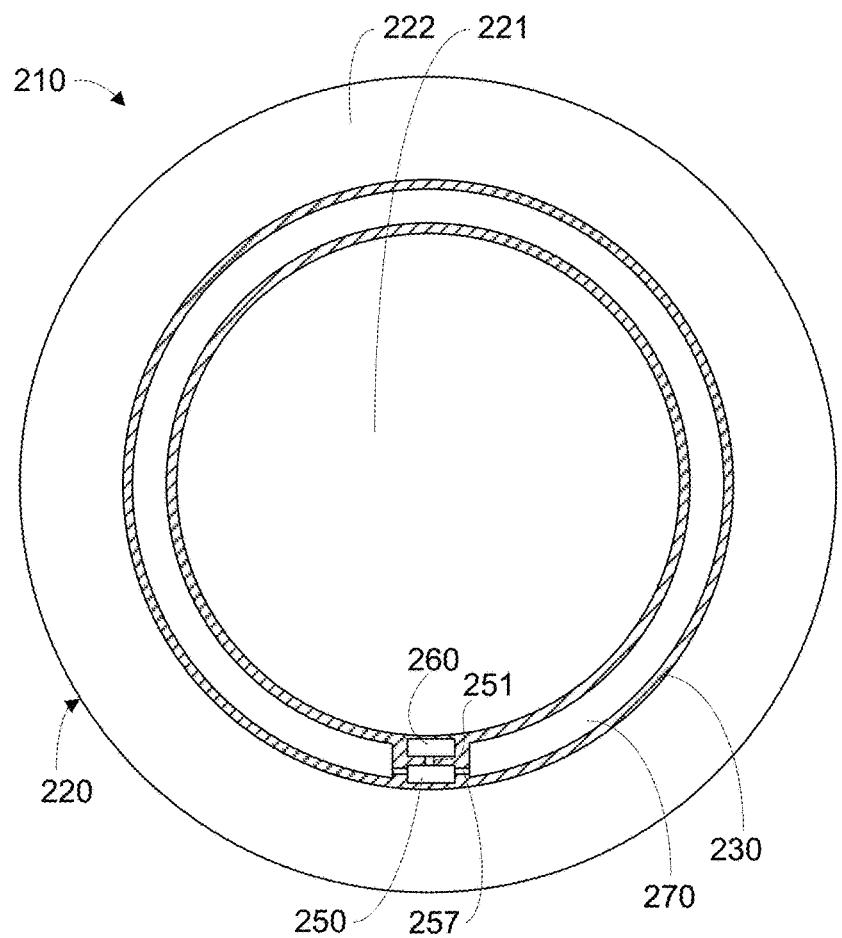
FIG. 2A is a bottom view of an example eye-mountable device.
Figure 2B:
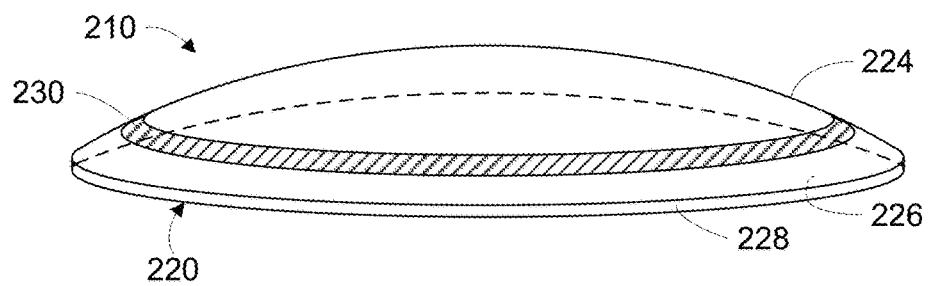
FIG. 2B is an aspect view of the example eye-mountable device shown in FIG. 2A.

FIG. 2A is a bottom view of an example eye-mountable electronic device 210 that includes an analyte sensor as configured as described herein. FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 220 can be formed with one side having a concave surface 226 suitable to fit over a corneal surface of an eye. The opposing side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved out of the page, whereas the center region 221, near the center of the disk is curved in to the page.

A substrate 230 is embedded in the polymeric material 220. The substrate 230 can be embedded to be situated along the outer periphery 222 of the polymeric material 220, away from the center region 221. The substrate 230 does not interfere with vision because it is too close to the eye to be in focus and is positioned away from the center region 221 where incident light is transmitted to the eye-sensing portions of the eye. Moreover, the substrate 230 can be formed of a transparent material to further mitigate any effects on visual perception.

The substrate 230 can be shaped as a circular ring (e.g., a disk with a central hole). The flat surface of the substrate 230 (e.g., along the radial width) is a platform for mounting electronics such as chips (e.g., via flip-chip mounting) and for patterning conductive materials (e.g., via deposition techniques) to form electrodes, antenna(e), and/or connections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an analyte sensor, etc.) can be formed from conductive materials patterned on the substrate 230 by a process for precisely patterning such materials, such as deposition, lithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the bio-interactive electronics module 260 is mounted to a side of the substrate 230 facing the concave surface 226. Where the bio-interactive electronics module 260 includes an analyte sensor, for example, mounting such a sensor on the substrate 230 to be close to the concave surface 226 allows the sensor to sense analyte concentrations in a tear film near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made via conductive materials passing through the substrate 230.

The loop antenna 270 can be a layer of conductive material patterned along the flat surface of the substrate to form a conductive ring or a plurality of concentric conductive rings. In some instances, the loop antenna 270 can be formed without making a complete loop. For instance, and the antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can be passed through the substrate 230 to the controller 250.

Figure 2D:
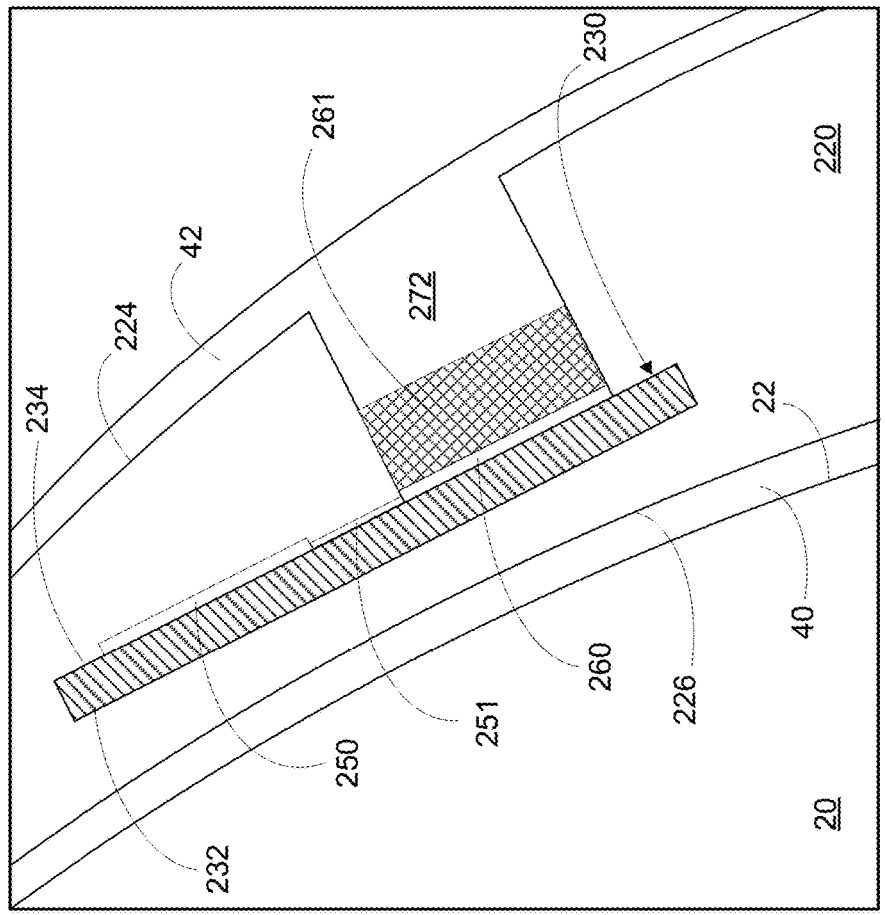
FIG. 2D is a side cross-section view enhanced to show the tear film layers surrounding the surfaces of the example eye-mountable device when mounted as shown in FIG. 2C.
Figure 2C:
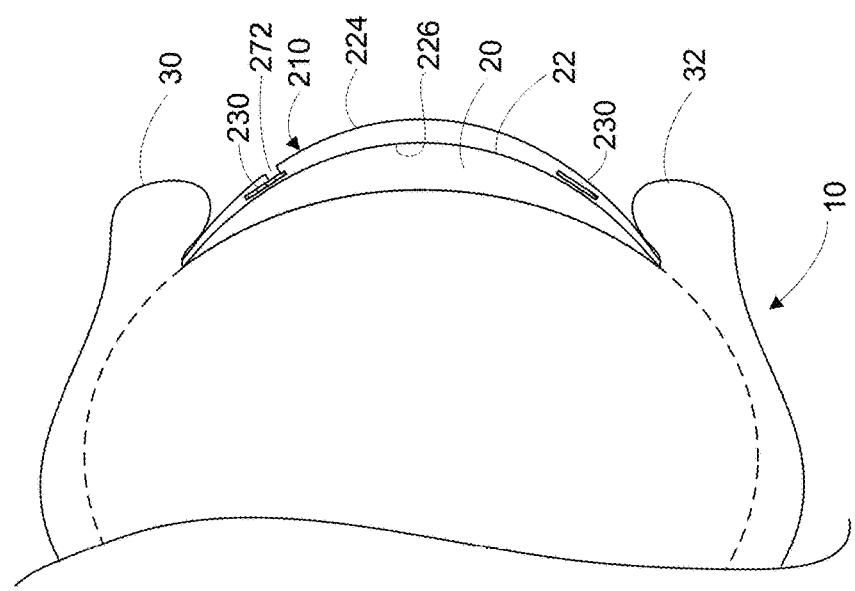
FIG. 2C is a side cross-section view of the example eye-mountable device shown in FIGS. 2A and 2B while mounted on a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226.

As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the outward-facing surface 234 such that the bio-interactive electronics 260 are relatively closer in proximity to the outer tear film layer 42 than if they were mounted on the inward-facing surface 232. With this arrangement, the bio-interactive electronics 260 can receive analyte concentrations in the outer tear film 42 through the channel 272. However, in other examples, the bio-interactive electronics 260 may be mounted on the inward-facing surface 232 of the substrate 230 such that the bio-interactive electronics 260 are facing the concave surface 226 and able to receive analyte concentrations from the inner tear film 40.

Bio-interactive electronics 260 can be made selectively sensitive to an analyte by localizing an analyte sensing component which selectively interacts with the analyte near an electrode of the bio-interactive electronics 260. As shown in FIG. 2D, a crosslinked, hydrophilic copolymer layer 261 can be located proximate to the electrode of the bio-interactive electronics 260. The copolymer layer 261 can be permeable to the analyte and contain the analyte sensing component that selectively interacts with the analyte to create analytes which can be sensed directly by the bio-interactive electronics 260. In some examples, the copolymer layer 261 is comprised of 2-hydroxyethyl methacrylate, 2,2-dimethoxy-2-phenylacetophenone, and di(ethylene glycol) dimethacrylate units and contains an analyte sensing component that includes an enzyme that selectively interacts with the analyte. In some embodiments, the enzyme embedded in the copolymer could be glucose oxidase In some embodiments, the body-mountable device could be a tooth-mountable device. The tooth-mountable device may take the form of or be similar in form to the eye-mountable device, and could be configured to detect at least one analyte in a fluid (e.g., saliva) of a user wearing the tooth-mountable device.

In some embodiments, the body-mountable device could comprise a skin-mountable device. The skin-mountable device could take the form of or be similar in form to the eye-mountable device, and could be configured to detect at least one analyte in a fluid (e.g., perspiration, blood, etc.) of a user wearing the skin-mountable device.

Although the crosslinked, hydrophilic copolymer layers in the above examples comprise methacrylate groups, there are a number of ethylenically unsaturated groups known in the art to be capable of undergoing polymerization. Ethylenically unsaturated monomers and macromers could be either acrylic- or vinyl-containing Vinyl-containing monomers contain the vinyl grouping ($CH_2=CH-$), and are generally highly reactive. Acrylic-containing monomers are represented by the formula:

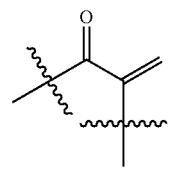 [SMILES: *C(=C)C(*)=O]

Examples of suitable polymerizable groups could include acrylic-, ethacrylic-, itaconic-, styryl-, acrylamido-, methacrylamido- and vinyl-containing groups such as the allyl group.

In addition to the above disclosed methods of forming crosslinked, hydrophilic copolymer layers by the polymerization of ethylenically unsaturated monomers and macromonomers, additional chemistries will be known to one of ordinary skill in the art to form such copolymer layers. As an example, epoxy chemistry, in which multifunctional amines and multifunctional epoxy compounds can be mixed together and cured, could be used to form crosslinked, hydrophilic copolymer layers. Additionally, urethane chemistry could be used, in which multifunctional isocyanates can be mixed with multifunctional alcohols and cured to provide crosslinked, hydrophilic copolymer layers. Other chemistries for the formation of crosslinked, hydrophilic copolymer layers exist, and will be well known to those of ordinary skill in the art.

III. Example Methods

Figure 3:
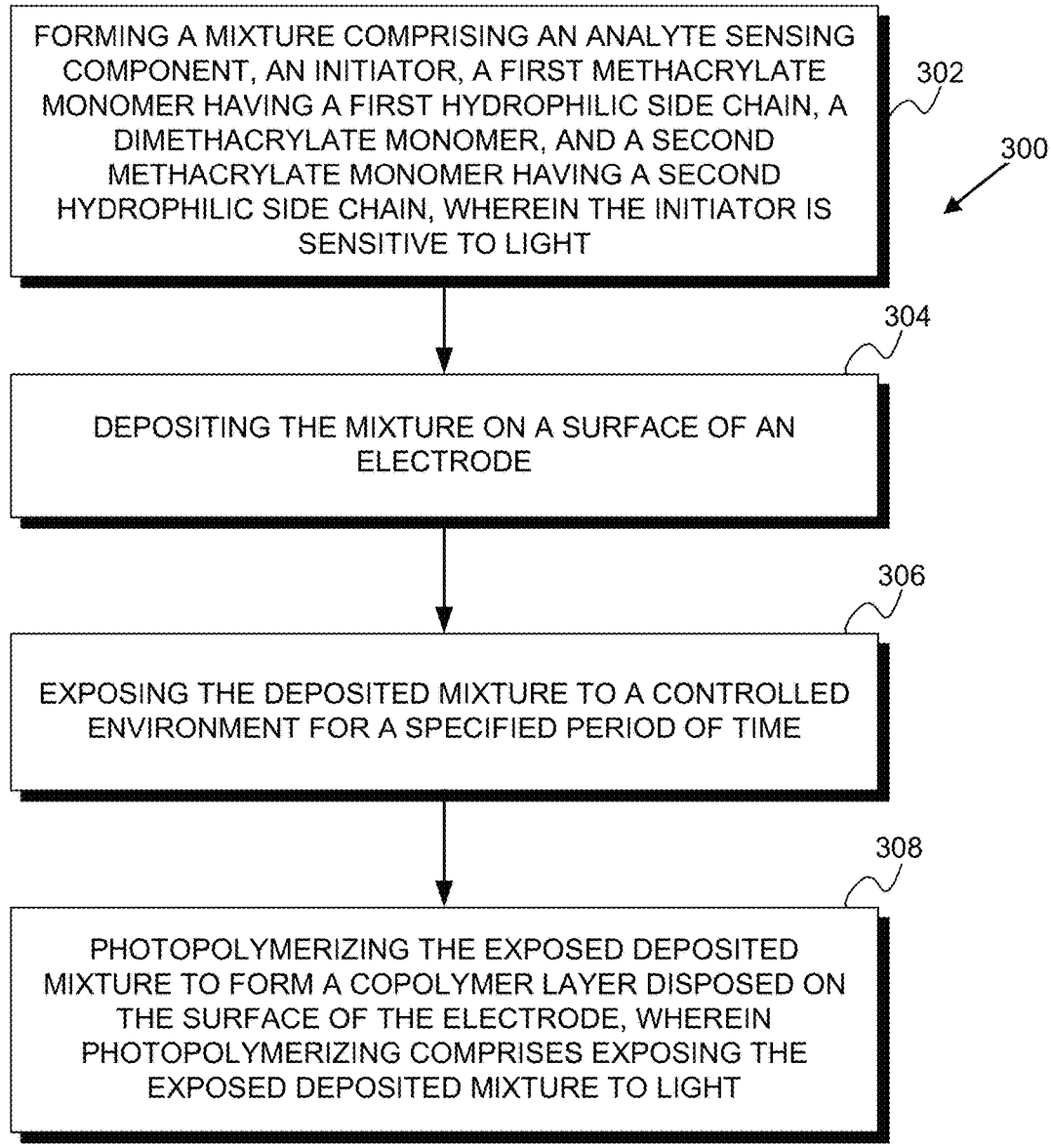
FIG. 3 is a flowchart of an example method.

FIG. 3 illustrates an example method for making an analyte sensor (300) that includes forming a mixture comprising an analyte sensing component, an initiator, a first methacrylate monomer having a first hydrophilic side chain, a dimethacrylate monomer, and a second methacrylate monomer having a second hydrophilic side chain, wherein the initiator is sensitive to light (302), depositing the mixture on a surface of an electrode (304), exposing the deposited mixture to a controlled environment for a specified period of time (306), and, after exposing the deposited mixture to the controlled environment for the specified period of time, photopolymerizing the exposed deposited mixture to form a copolymer layer disposed on the surface of the electrode, wherein photopolymerizing comprises exposing the exposed deposited mixture to light (308).

In some embodiments, forming a mixture (302) could include forming a mixture on the surface of the electrode. For example, each component of the mixture, or a combination of one or more components of the mixture, could be individually deposited on the surface of the electrode to form the mixture. A number of separate solutions, each containing amounts of some or all of the components of the mixture, could be formed separately and then individually deposited on the surface of the electrode to form the mixture.

The ratio of components in the mixture can be chosen to control a desired property or properties of the analyte sensor. For example, the amount of the second methacrylate monomer having a second hydrophilic side chain in the mixture could be chosen to affect a porous network of the crosslinked, hydrophilic copolymer layer. Controlling the properties of the porous network could allow for controlling the permeability of the analyte sensor to the analyte. Other properties of the analyte sensor could be controlled by adjusting the amount of the mixture deposited on the electrode, and/or adjusting the ratio of the amount of the second methacrylate monomer in the mixture and the amount of the first methacrylate monomer in the mixture.

The mixture, or precursor solutions of the mixture, could be formed in an aqueous medium, alcoholic medium, or a mixture of aqueous and alcoholic media. The aqueous medium can include a buffered aqueous solution, for example, a solution including citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino)succinic acid, or phosphate buffered saline (PBS). In some embodiments, the mixture, or precursor solutions of the mixture, could be formed in a mixture of a buffered aqueous solution and ethanol.

In some embodiments of the method (300), first, second and third solutions could be formed with approximately the same concentration of analyte sensing component, first methacrylate monomer, and second methacrylate monomer, respectively. The percentage of each component in the mixture can then be controlled by adjusting the amounts of each of the three solutions used to form the mixture. In some instances, the percentage of analyte sensing component in the mixture is about 20% by weight to about 50% by weight, the percentage of first methacrylate monomer is 20% by weight to about 60% by weight, and the percentage of second methacrylate monomer is about 10% by weight to about 40% by weight. All percentages are given as a percentage of the cumulative amount of analyte sensing component, first methacrylate monomer and second methacrylate monomer in the mixture. In certain examples, the percentage of analyte sensing component is about 40%, the amount of first methacrylate monomer is about 35% to about 40%, and the amount of second methacrylate monomer is about 20% to about 25%. In certain embodiments, the mixture is thoroughly mixed, optionally with a stirrer or shaker, before being deposited onto the surface of the electrode.

In some embodiments, the analyte sensing component could be an enzyme that reacts selectively with the analyte. The analyte sensing component of the mixture could be selected to sense physiological levels of a specific analyte in a fluid to which the analyte sensor could be exposed. For example, glucose, lactate, cholesterol and various proteins and lipids can be found in body fluids, including, for example, tear film, and can be indicative of medical conditions that could benefit from continuous or semi-continuous sensing by an analyte sensor.

The analyte sensing component can be an enzyme selected to be sensitive to one or more analytes. For example, cholesterol levels could be sensed with cholesterol oxidase, lactate levels with lactate oxidase, and glucose levels with glucose oxidase or glucose dehydrogenase (GDH).

In some embodiments, the analyte sensing component can be an enzyme that mediates a chemical reaction of an analyte to produce detectable reaction products. In some embodiments, the analyte sensing component is glucose dehydrogenase (GDH). In certain instances, a selected analyte sensing component can require cofactors in order to sense the analyte. The cofactors could be included in the mixture. Cofactors could include flavin adenine dinucleotide (FAD), thiamine pyrophosphate (TPP), nicotinamide adenine dinucleotide (NAD), flavin mononucleotide (FMN), pyrroloquinoline quinone (PQQ) or a coenzyme. In embodiments incorporating glucose oxidase, FAD could be included. In embodiments incorporating pyruvate oxidase, FAD and TPP could be included.

The first and second methacrylate monomers include hydrophilic side chains that can have one or more heteroatoms. The first and second side chains could include one or more alkylene oxide units.

In some embodiments of the method, the first methacrylate monomer has the structure of formula (IV):

(IV)

where R is a hydrophilic group. In certain embodiments of the method, the hydrophilic group includes one or more hydroxy groups, such as an alcohol.

In some embodiments of the method, the first methacrylate monomer has the structure of formula (IVa):

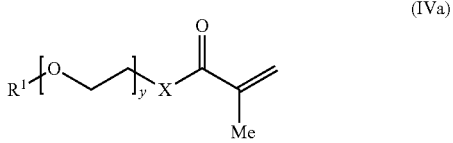

(IVa)

where X, y, $R^1$, and R' are selected to provide the first methacrylate-derived monomeric unit of the crosslinked, hydrophilic copolymer described herein.

In some embodiments of the method, the first methacrylate monomer has the structure:

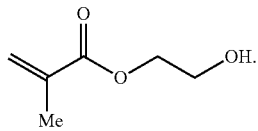

In some embodiments of the method, the second methacrylate monomer has the structure of formula (V):

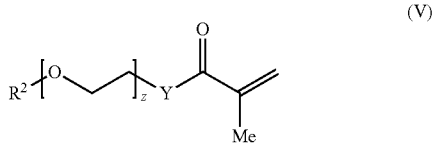

(V)

where Y, z, $R^2$ and R' are selected to provide the second methacrylate-derived monomeric unit of the crosslinked, hydrophilic copolymer described herein.

In some embodiments of the method, the second methacrylate monomer has the structure of formula (Va):

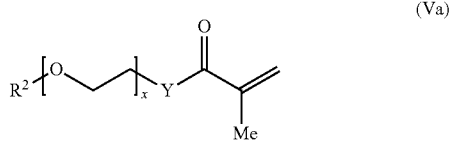

(Va)

where x has a number of different values. In some embodiments of the method, the second methacrylate monomer has a number of different values for x such that the poly(ethylene glycol) component of the second methacrylate monomer has a number average molecular weight ($M_n$) of about 100 daltons to about 10,000 daltons. In certain embodiments, the values of x are selected so that the $M_n$ of the poly(ethylene glycol) component of the second methacrylate monomer falls within a range in Table 1.

In certain embodiments of the method (300), the second methacrylate monomer has the structure of formula (Va), where Y is —O—, $R^2$ is methyl and x has a number of different values such that the poly(ethylene glycol) component of the second methacrylate monomer has a number average molecular weight ($M_n$) of about 500.

The dimethacrylate monomer is a molecule having two terminal methacrylate groups tethered by a hydrophilic linker. The hydrophilic linker is selected to provide crosslinks between third methacrylate-derived units in different backbone chains of a crosslinked, hydrophilic copolymer layer that will be formed from the mixture. In embodiments where the mixture is formed from a combination of two or more precursor solutions each having a dimethacrylate monomer, the dimethacrylate monomers can be the same, or in some instances, can be different.

The extent of crosslinking in the crosslinked, hydrophilic copolymer layer that will be formed from the mixture can be controlled by adjusting the amount of dimethacrylate monomer in the mixture. In some embodiments, the dimethacrylate monomer is about 1% to about 15% of the mixture. In other examples, the amount is about 1% to about 5%, or about 5% to about 10%, or about 10% to about 15%. In some embodiments, the amount is about 1%. In some instances, both the precursor solutions of the mixture include about 1% of the dimethacrylate monomer in the mixture.

In some embodiments of the method, the dimethacrylate monomer includes one or more alkylene oxide units to provide the crosslinks of the crosslinked, hydrophilic copolymer layer that will be formed from the mixture. In some embodiments, the dimethacrylate monomer includes a poly(ethylene glycol) (PEG) component. For example, the dimethacrylate monomer can have the structure of formula (VI):

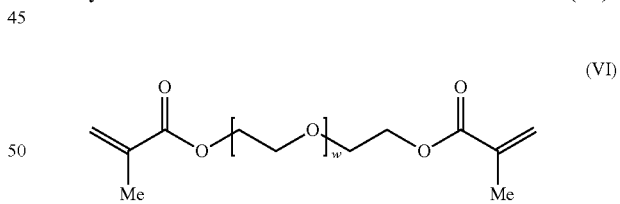

(VI)

where w is 0, 1, 2, 3, 4, 5, 6, 7, 8, 9 or 10.

In certain embodiments, the dimethacrylate monomer can have a number of different values for w. In certain embodiments, the dimethacrylate monomer can have a number of different values for w such that the PEG component of the dimethacrylate monomer has a number average molecular weight of from about 2 to about 250.

In other embodiments of the method (300), the dimethacrylate monomer can have the structure of formula (VI) where w has a number of different values such that the PEG component of the methacrylate monomer has a number average molecular weight ($M_n$) of about 100 daltons to about 10,000 daltons. In certain embodiments, the values of w are selected such that the $M_n$ of the PEG component of the dimethacrylate monomer falls within a range in Table 2. In some embodiments, the dimethacrylate monomer is di(ethylene glycol) dimethacrylate.

Depositing the mixture onto the surface of the electrode (304) could be accomplished by a number of methods. For example, the depositing could be performed manually with a micro-syringe, or by automated fabrication processes with nano jet or some other dispensing equipment.

In some embodiments of the method (300), the amount of the mixture deposited onto the surface of the electrode is selected to provide a desired thickness of the crosslinked, hydrophilic copolymer layer of the analyte sensor. In some embodiments, the volume of the mixture deposited is specified based on an area of the surface of the electrode. In some embodiments, the volume of the mixture deposited on the electrode is about 50 nL/mm$^2$ to about 500 nL/mm$^2$. In some embodiments, the volume of the mixture deposited on the surface of the electrode is 150 nL/mm$^2$. In some instances, depositing about 100 nL/mm$^2$ of the mixture on the electrode, exposing the deposited mixture to a controlled environment for a specified period of time, and photopolymerizing the exposed deposited mixture could provide a crosslinked, hydrophilic copolymer layer that is less than about 20 μm in thickness.

Exposing the deposited mixture to a controlled environment for a specified period of time (306) could encompass exposing the deposited mixture to a variety of controlled environments. For example, the deposited mixture could be exposed to an open air environment. The open-air environment could have one or more of a standard temperature, pressure, or humidity. In some embodiments, the deposited mixture could be exposed to an environment having one or more or a controlled pressure, a controlled temperature, or a controlled humidity. In some embodiments, the deposited mixture could be exposed to an environment having a controlled partial pressure of one or more gases. The one or more gases could include oxygen, nitrogen, carbon dioxide, a noble gas, or some other gas or gases according to an application. In some embodiments, the controlled environment could be a total vacuum or a partial vacuum. In some embodiments, the controlled environment could include a controlled convection current of a gas or gases; the controlled convection current could be directed toward the deposited mixture, parallel to a plane of the electrode onto which the mixture is deposited, or any other relation to the deposited mixture according to an application.

Aspects of the controlled environment could be chosen to effect a specified change in the deposited mixture. For example, aspects of the controlled environment could be chosen to effect a controlled rate of evaporation of one or more components in the mixture. Different components of the deposited mixture could have different controlled rates of evaporation effected by chosen aspects of the controlled environment.

Exposing the deposited mixture to a controlled environment for a specified period of time (306) could encompass exposing the deposited mixture for a variety of periods of time. Further, the specified period of time could be specified based on variety of considerations. The specified period of time could be a period of time between 0 and 60 minutes. The specified period of time could be 5 minutes.

The specified time could be based on a desired analyte sensor thickness. For example, the controlled environment could be such that one or more components of the deposited mixture evaporates, reducing over time the volume of the mixture remaining on the surface of the electrode. The specified time could be specified such that the volume of deposited mixture remaining on the surface of the electrode after the specified time is such that, after photopolymerizing the exposed deposited mixture into a crosslinked, hydrophilic copolymer layer, the copolymer layer has a desired thickness.

The specified time could be based on a desired concentration profile of the analyte sensing component within the analyte sensor. For example, the composition of the components of the mixture could be such that the analyte sensing component is not in equilibrium within the mixture; that is, over time, the analyte sensing component could settle toward the bottom of the deposited mixture, such that the sensing component, over time, comes to have a higher concentration at the bottom of the mixture than at the top of the mixture. The mixture could be deposited on the surface of the electrode such that the bottom of the mixture corresponded to a region of the analyte sensor where it was desired to have a higher concentration of the analyte sensing component. The specified time could be specified such that a desired concentration profile of the analyte sensing component within the deposited mixture, corresponding to a desired concentration profile of the analyte sensing component in the analyte sensor, had developed by the end of the specified time.

The specified time could be based on a desired analyte sensor sensitivity. As described elsewhere in this disclosure, the sensitivity of an analyte sensor made using methods described herein could be affected by factors including but not limited to the thickness of a copolymer layer containing an analyte sensing component and the concentration profile of an analyte sensing component within a copolymer layer containing the analyte sensing component. The specified period of time could be specified such that, in view of the properties of the components of the deposited mixture and the properties of the controlled environment to which the deposited mixture could be exposed, a volume of the deposited mixture could be evaporated. The volume of the remaining deposited mixture could, when photopolymerized, result in a copolymer layer having a thickness corresponding to a desired analyte sensor sensitivity. The specified period of time could be specified such that, in view of the properties of the components of the deposited mixture and the properties of the controlled environment to which the deposited mixture could be exposed, a concentration profile of the analyte sensing component within the deposited mixture could be achieved, where the concentration profile of the analyte sensing component within the exposed deposited mixture was higher proximate the electrode. The concentration profile of the analyte sensing component within the exposed deposited mixture could, when photopolymerized, result in a copolymer layer having a concentration profile of the analyte sensing component corresponding to a desired analyte sensor sensitivity. Other properties or factors of the controlled environment, the mixture, the depositing of the mixture, or other aspects of the analyte sensor could be considered when specifying a period of time to expose the deposited mixture to the controlled environment so as to achieve a desired analyte sensitivity.

Photopolymerizing the exposed deposited mixture to form a copolymer layer disposed on the surface of the electrode, wherein photopolymerizing comprises exposing the exposed deposited mixture to light (308) could include a variety of conditions for photopolymerization and/or types of light. Conditions suitable to photopolymerize (i.e., cure) the exposed deposited mixture can be selected based on the characteristics of the initiator and the monomers being polymerized, and so as not to degrade the analyte sensing component. In embodiments where the analyte sensing component is an enzyme, the temperature and pH of the exposed deposited mixture during photopolymerization can be controlled to preserve the activity of the enzyme. Further, the wavelength, intensity, and duration of the light used to expose the exposed deposited mixture can be selected to preserve the activity of the enzyme. In certain embodiments the initiator is activated with ultraviolet (UV) light. For example, when 2,2-diemthoxy-2-phenylacetophenone is used as an initiator, photopolymerization can be performed with UV light. In embodiments where the mixture is formed from the combination of two or more precursor solutions each including an initiator, the initiators can be the same, or in some instances, can be different.

The analyte sensing component can be present during photopolymerization of the methacrylate and dimethacrylate monomers in the exposed deposited mixture, such that polymerization of the methacrylate and dimethacrylate monomers results in the formation of a crosslinked, copolymer network in which the analyte sensing component is embedded. The embedded analyte sensing component could be immobilized and could be used to sense a corresponding analyte of interest.

IV. Example Implementations

In a first example implementation, three solutions (S1, S2, S3) were prepared:
S1) 25 mg/ml glucose oxidase (GOx) in PBS buffer (pH=7.4)
S2) 2-hydroxyethyl methacrylate monomer solution containing 1% by weight di(ethylene glycol) dimethacrylate and 1% by weight 2,2-dimethoxy-2-phenylacetophenone.
S3) poly(ethylene glycol) methyl ether methacrylate (average Mn 500, Aldrich product #447943) monomer solution containing 1% by weight di(ethylene glycol) dimethacrylate and 1% by weight 2,2-dimethoxy-2-phenylacetophenone.

Two formulations (F2 and F4) were prepared by combining a volume of each solution (S1, S2, S3) according to the ratios in the following table:

|  | S1 | S2 | S3 |
| --- | --- | --- | --- |
| Formulation F2 | 0.40 | 0.40 | 0.20 |
| Formulation F4 | 0.40 | 0.35 | 0.25 |

The resulting formulations were thoroughly mixed with a vortex shaker. A micro-syringe was used to deposit 100 nL/mm$^2$ of each formulation onto an electrode, and the deposited solution was photopolymerized using ultraviolet light for 5 minutes at 365 nm under nitrogen with an EC-500 light exposure chamber (Electro-Lite Corp). The resulting photopolymerized crosslinked copolymers each had a thickness of about 20 μm. The sensor made with Formulation F4, used a greater ratio of solution S3 to solution S2 than Formulation F2. Thus, the sensor made with Formulation F4 had a greater ratio of poly(ethylene glycol) methyl ether methacrylate-derived units to 2-hydroxyethyl methacrylate-derived units than the sensor made with Formulation F2.

Figure 4:
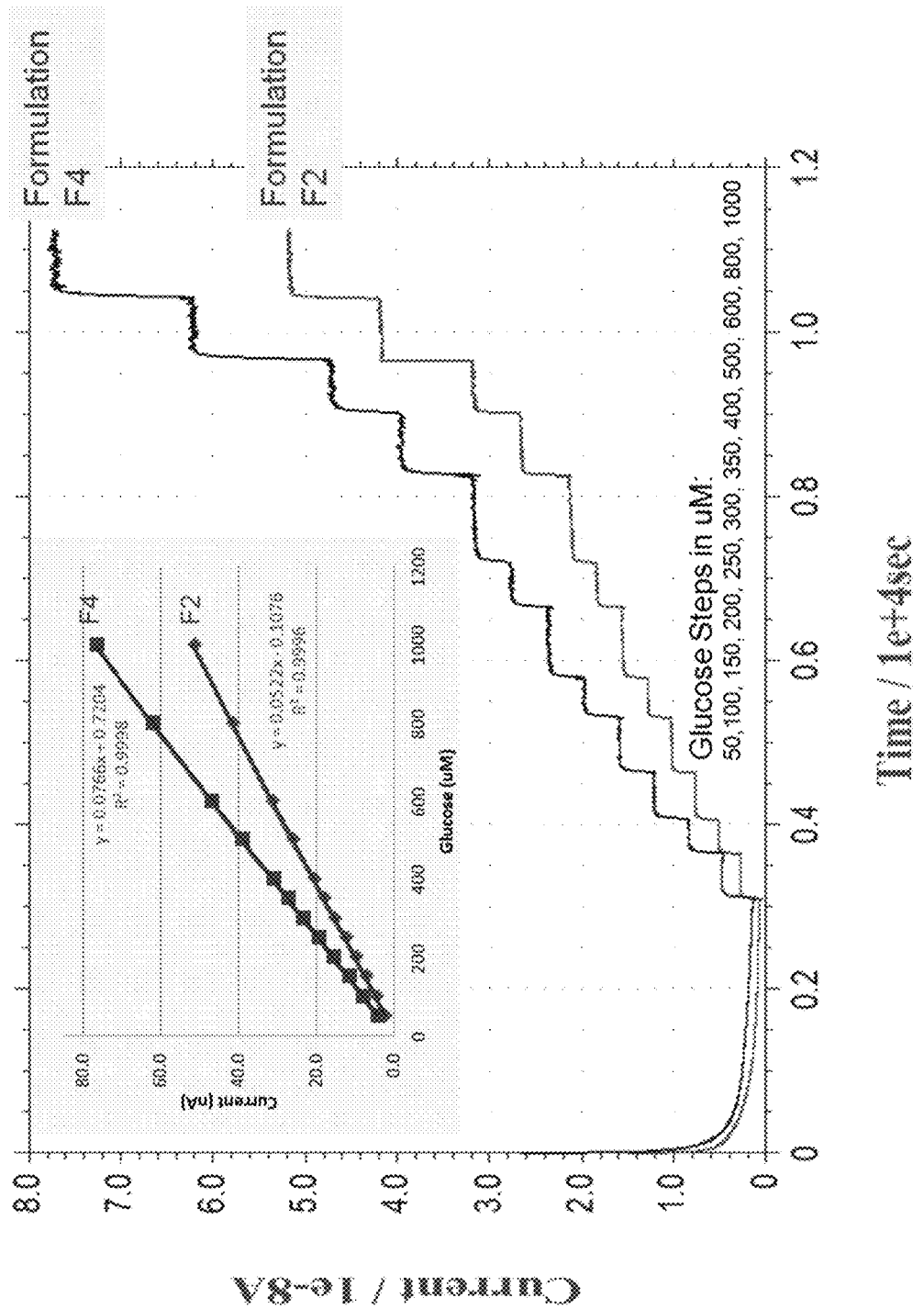
FIG. 4 is a graph of current produced by example analyte sensors.

The analyte sensors of Formulation F2 and F4 were tested by being exposed to solutions of glucose in phosphate buffered saline (PBS) having glucose concentrations ranging from 20 μM to 1000 μM. Both sensors were submerged in a PBS solution and the glucose concentration was increased every 10-15 minutes. The current generated at the electrode was measured using a potentiostat. A linear relationship between current and glucose concentration was observed for both formulations (See inset, FIG. 4). The sensor made with Formulation F4, which was a greater ratio of poly(ethylene glycol) methyl ether methacrylate-derived units to 2-hydroxyethyl methacrylate-derived units than the sensor made with Formulation F2, had a higher current response at the same concentration of glucose, and thus a higher sensitivity to glucose, than the sensor made with Formulation F2. See FIG. 4.

Figure 5:
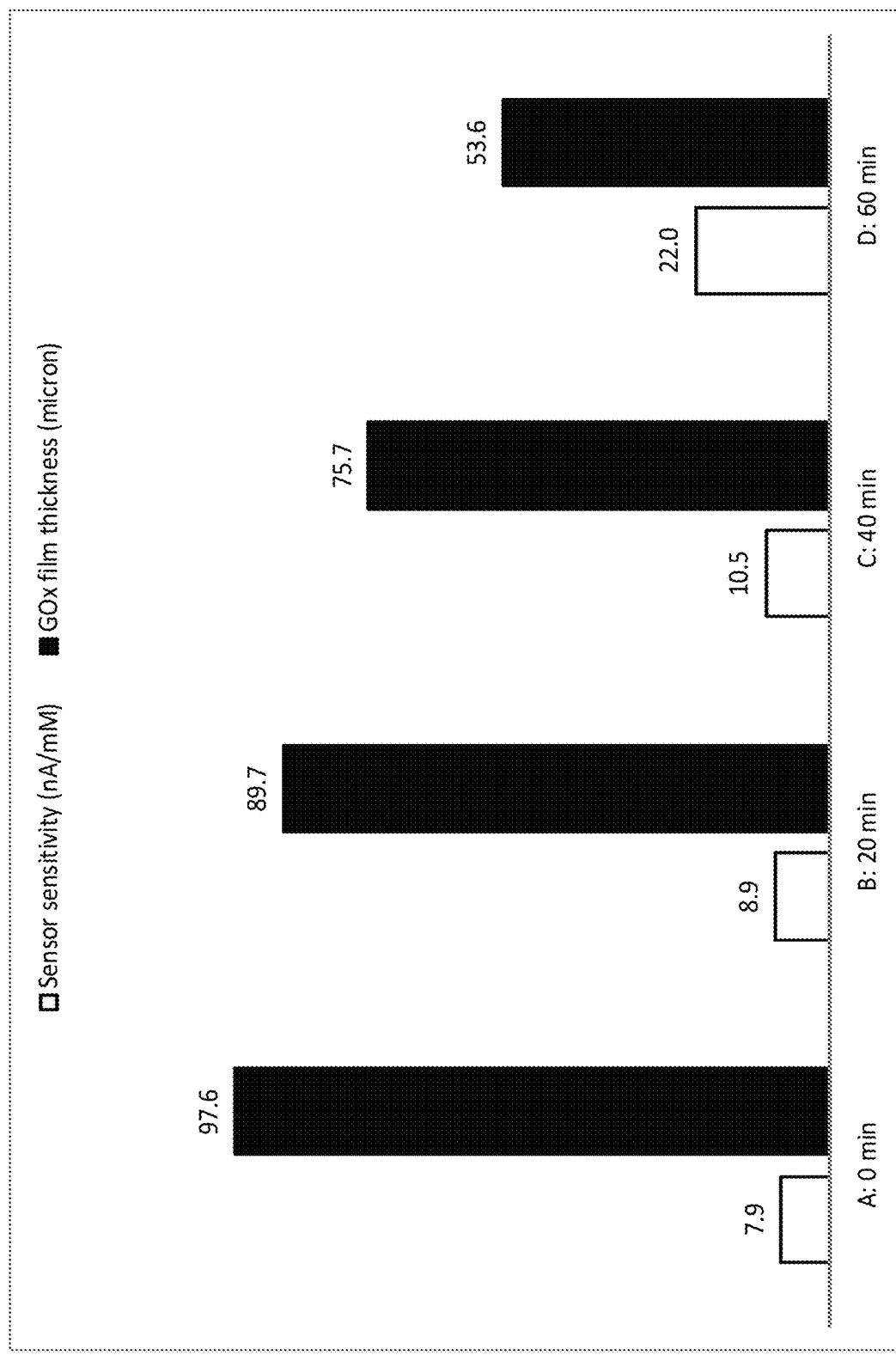
FIG. 5 is a graph of the sensitivity and thickness of example analyte sensors.

In a second example implementation, four sensors (A-D) were made from a mixture that included glucose oxidase, a first methacrylate monomer having a first hydrophilic side chain, a dimethacrylate monomer, an initiator that was sensitive to light, and a second methacrylate monomer having a second hydrophilic side chain. Each sensor included an identical electrode, and identical amounts of the mixture were deposited on each of the four electrodes. Each sensor was then exposed to the open air for a different period of time, sensors A, B, C, and D were exposed for 0, 20, 40, and 60 minutes, respectively (see FIG. 5). The sensors were then identically photopolymerized as described herein, resulting in the polymerization of the exposed deposited mixtures into crosslinked, hydrophilic copolymer layers disposed on the electrodes. The sensors were then exposed to solutions of glucose in phosphate buffered saline (PBS) and the current generated at the electrode was measured using a potentiostat. Their sensitivities to glucose were determined by varying the concentration of the glucose in the PBS and using the potentiostat to measure the corresponding levels of current. The sensitivity of the electrodes increased with increasing exposure time; see FIG. 5. The thicknesses of the copolymer layers were also measured. The thickness of the copolymer layer decreased with increasing exposure time; see FIG. 5.

CONCLUSION

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

What is claimed is:

1. A method, comprising:
depositing a mixture on a surface of an electrode, wherein the mixture comprises an analyte sensing component, an initiator, a first methacrylate monomer having a first hydrophilic side chain, a dimethacrylate monomer, and a second methacrylate monomer having a second hydrophilic side chain, wherein the initiator is sensitive to light;
exposing the deposited mixture to a controlled environment for a specified period of time; and
photopolymerizing the exposed deposited mixture to form a copolymer layer disposed on the surface of the electrode, whereby the analyte sensing component has a non-uniform concentration in the formed copolymer layer such that the concentration is higher proximate the surface of the electrode, wherein photopolymerizing comprises exposing the exposed deposited mixture to light.

2. The method of claim 1, wherein the controlled environment is an open-air environment.

3. The method of claim 1, wherein the controlled environment has at least one of a controlled pressure, a controlled humidity, or a controlled temperature.

4. The method of claim 1, wherein the specified period of time is between 0 minutes and 60 minutes.

5. The method of claim 4, wherein the specified period of time is 5 minutes.

6. The method of claim 1, wherein the specified period of time is specified based on a desired analyte sensor thickness.

7. The method of claim 1, wherein the specified period of time is specified based on a desired concentration profile of the analyte sensing component within the copolymer layer disposed on the surface of the electrode.

8. The method of claim 1, wherein the specified period of time is specified based on a desired analyte sensor sensitivity.

9. The method of claim 1, wherein depositing the mixture on a surface of an electrode comprises depositing a specified volume of the mixture, wherein the specified volume of the mixture is based on an area of the surface of the electrode.

10. The method of claim 9, wherein the specified volume of the mixture based on the area of the surface of the electrode is between 50 nL and 150 nL of mixture per square millimeter of electrode surface.

11. The method of claim 10, wherein the specified volume of the mixture based on the area of the surface of the electrode is 100 nL of mixture per square millimeter of electrode surface.

12. The method of claim 1, wherein the first methacrylate monomer has the structure of formula (I):

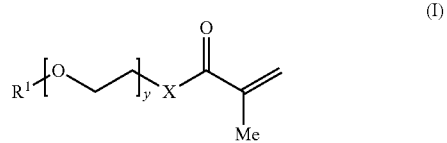

wherein
X is —O—, —NR'— or —S—;
y is 0-10; and
$R^1$ is hydrogen, —$C_1$-$C_{12}$alkyl, —$C_1$-$C_{12}$alkyl-OH, —SiR'$_3$, —$C_1$-$C_{12}$alkyl-C(O)OR', wherein R' is —$C_1$-$C_{12}$alkyl.

13. The method of claim 1, wherein the second methacrylate monomer has the structure of formula (II):

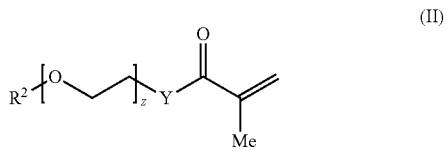

wherein
Y is —O—, —NR'— or —S—;
$R^2$ is hydrogen, —$C_1$-$C_{12}$alkyl, —SiR'$_3$, —C(O)—$C_1$-$C_{12}$alkyl, —$C_1$-$C_{12}$alkyl-C(O)OR', where R' is hydrogen or —$C_1$-$C_{12}$alkyl; and
z is an average value of from about 2 to about 250.

14. The method of claim 1, wherein the dimethacrylate monomer has a structure of formula (III):

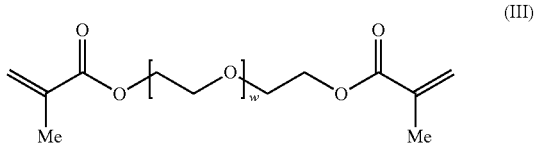

wherein w is an average value of from about 2 to about 250.

15. The method of claim 1, wherein the analyte sensing component is glucose oxidase.

16. The method of claim 1, wherein the light is ultraviolet light.

17. The method of claim 1, wherein the initiator is 2,2-dimethoxy-2-phenylacetophenone.

18. An analyte sensor comprising:
an electrode;
a layer on a surface of the electrode, wherein the layer comprises:
a crosslinked, hydrophilic copolymer; and
an analyte sensing component embedded within the crosslinked, hydrophilic copolymer, wherein the analyte sensing component has a non-uniform concentration in the layer, such that the concentration is higher proximate the surface of the electrode, wherein the crosslinked, hydrophilic copolymer comprises backbone chains comprising:
first methacrylate-derived units, each having a first hydrophilic side chain;
second methacrylate-derived units, each having a second hydrophilic side chain, wherein the first and second side chains are the same or different;
third methacrylate-derived units; and
hydrophilic crosslinks between third methacrylate-derived units in different backbone chains.

19. The sensor according to claim 18, wherein the analyte sensing component comprises glucose oxidase.

20. The sensor according to claim 18, wherein the layer has a thickness of less than 20 µm.

21. The sensor according to claim 18, wherein the first methacrylate-derived units have the structure of formula (IV):

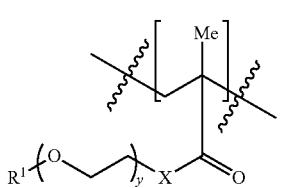

(IV)

wherein
X is —O—, —NR'— or —S—;
y is 0-10; and
$R^1$ is hydrogen, —$C_1$-$C_{12}$alkyl, —$SiR'_3$, —$C_1$-$C_{12}$alkyl-C(O)OR', wherein R' is —$C_1$-$C_{12}$alkyl.

22. The sensor according to claim 18, wherein the first methacrylate-derived units have the structure:

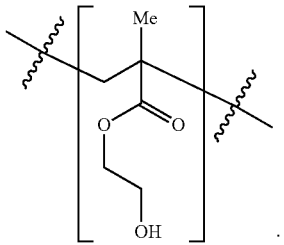

23. The sensor according to claim 18, wherein the second methacrylate-derived units have the structure of formula: (V):

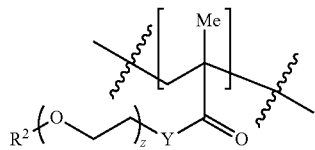

(V)

wherein
Y is —O—, —NR'— or —S—;
$R^2$ is hydrogen, —$C_1$-$C_{12}$alkyl, —$SiR'_3$, —C(O)—$C_1$-$C_{12}$alkyl, —$C_1$-$C_{12}$alkyl-C(O)OR', where R' is hydrogen or —$C_1$-$C_{12}$alkyl; and
z is an average value of from 2 to about 250.

24. The sensor according to claim 18, wherein the hydrophilic crosslinks have the structure of formula (VI):

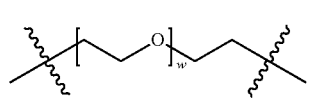

(VI)

wherein w is an average value of from about 2 to about 250.

25. The sensor according to claim 18, wherein
the first methacrylate-derived units are derived from 2-hydroxyethylmethacrylate;
the second methacrylate-derived units have the structure of formula (VII):

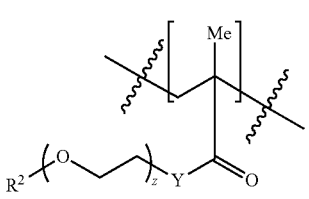

(VII)

wherein
Y is —O—, —NR'— or —S—;
$R^2$ is hydrogen, —$C_1$-$C_{12}$alkyl, —$SiR'_3$, —$C_1$-$C_{12}$alkyl-C(O)OR',
where R' is hydrogen or —$C_1$-$C_{12}$alkyl; and
z is an average value of from about 10 to about 15;
the hydrophilic crosslinks have the structure of formula (VIII):

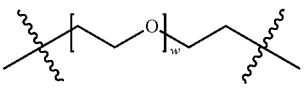

(VIII)

wherein w is 2; and
the analyte sensing component comprises glucose oxidase.

* * * * *